United States Patent [19]

Petrow et al.

[11] 4,295,985

[45] Oct. 20, 1981

[54] METHOD OF REMOVAL OF CHLORINE RETAINED BY HUMAN SKIN AND HAIR AFTER EXPOSURE TO CHLORINATED WATER, AND SOAP AND SHAMPOO COMPOSITIONS ADAPTED TO EFFECT SAID REMOVAL

[76] Inventors: Henry G. Petrow, 32 Garfield St.; Mark L. Weissman, 742 Belmont St., both of Watertown, Mass. 02172

[21] Appl. No.: 145,681

[22] Filed: May 1, 1980

Related U.S. Application Data

[63] Continuation-in-part of Ser. No. 88,144, Oct. 25, 1979, abandoned, which is a continuation of Ser. No. 900,601, Jun. 7, 1978, abandoned.

[51] Int. Cl.$^3$ .......................... C11D 7/32; D06L 3/10
[52] U.S. Cl. .................................... 252/105; 252/117; 252/121; 252/188; 134/2; 134/42; 424/149
[58] Field of Search ............... 252/105, 188, 121, 117; 134/2, 42; 424/149

[56] References Cited

U.S. PATENT DOCUMENTS 3,666,690  5/1972  Bann ............................... 252/105 X
3,808,194  4/1974  Raley ................................ 252/105

FOREIGN PATENT DOCUMENTS 2381 of 1857 United Kingdom ............... 252/105
Ad.1857N
115110  2/1918  United Kingdom ............... 252/105
1117930  6/1968  United Kingdom ............... 252/105

*Primary Examiner*—Mayer Weinblatt
*Attorney, Agent, or Firm*—Wolf, Greenfield & Sacks

[57] ABSTRACT

This disclosure deals with removing rapidly chlorine retained by the skin and hair of, for example, swimmers, after exposure to chlorinated water by means of a stoichiometric excess of a suitable reducing agent, such as an alkali thiosulfate and the like in aqueous solution, and with toilet soaps and shampoos comprising said agent adapted to effect said removal.

10 Claims, No Drawings

METHOD OF REMOVAL OF CHLORINE RETAINED BY HUMAN SKIN AND HAIR AFTER EXPOSURE TO CHLORINATED WATER, AND SOAP AND SHAMPOO COMPOSITIONS ADAPTED TO EFFECT SAID REMOVAL

RELATED APPLICATIONS

This application is a continuation-in-part of application Ser. No. 88,144, filed Oct. 25, 1979 now abandoned which is a continuation of application Ser. No. 900,601 filed June 7, 1978 and now abandoned.

BACKGROUND OF THE INVENTION

This invention relates to the removal of chlorine retained by human skin and hair after exposure to chlorinated water, and to a cleansing toilet soap or detergent composition adapted to remove retained chlorine from human skin and hair.

The operators of the thousands of indoor and outdoor swimming pools owned by clubs, schools, motels, cities, and towns, and others usually chlorinated the water in accordance with the standard health regulations. It is a common complaint by swimmers that their skin and hair retain chlorine which can cause irritations and which leaves a persistent disagreeable chlorine odor for long periods of time, even after thorough, lengthy, excessive and wasteful use of soap and/or shampoo in showering or bathing after a swim. To the best of our knowledge, this problem has not been solved heretofore. The common widely-used deodorant soaps can at best mask the chlorine odor temporarily without eliminating the chlorine.

SUMMARY OF THE INVENTION

It is an object of this invention to provide methods of removing chlorine retained by human skin and hair after exposure of chlorinated water which methods are rapid and efficient.

It is another object of this invention to provide chlorine reducing agents in combination with soap, detergents or shampoos which provide for rapid and efficient removal of chlorine from the skin and hair of humans by application to skin for relatively short periods of time.

According to the invention a method of rapidly removing retained chlorine from human skin and hair after immersion in chlorine-containing waters, comprises contacting the skin and hair substantially at room temperature with a water soluble, non-toxic and harmless to skin, chlorine reducing agent, with the chlorine reducing agent preferably in an amount of at least 3 times an excess of the stoichiometric amount required to reduce chlorine normally contained on the skin, to chloride. Preferably the skin and hair are contacted with a toilet soap, detergent or shampoo composition admixed with the chlorine reducing agent and water. The soap or detergent is preferably in solid form. A liquid aqueous shampoo composition for cleansing and removing retained chlorine from human skin and hair after immersion in chlorine-containing waters preferably consists essentially of a chemically stable, uniform mixture of a shampoo and a water soluble, non-toxic and harmless to skin chlorine reducing agent. The chlorine reducing agent is preferably present in an amount of from about 2% to 15% of detergent in the shampoo and from about 0.4% to 6% by weight of the entire liquid composition which comprises a detergent and water.

DESCRIPTION OF PREFERRED EMBODIMENTS

Usually, the chlorine content, as dissolved chlorine or hypochlorite, of swimming pool water is of the order of one-half to four parts per million. Unexpectedly, we have found that human skin and hair selectively extract chlorine from such water; that the chlorine retained by the skin and hair is strongly held and chemically much less reactive than chlorine or hypochlorite in dilute aqueous solution; and that the rapid reduction to harmless and odorless chloride of chlorine retained by skin and hair requires much more drastic reducing action than the known reduction to chlorides of aqueous chlorine or hypochlorite solutions. as shown in the following experiments.

Experiment I

Two identical solutions of sodium hypochlorite, each having a volume of three liters, and containing 15 ppm of chlorine (as hypochlorite) were prepared. In one solution, a hand and hairy forearm with an exposed skin area of the order of one square foot were immersed at room temperature for 30 seconds, then removed from solution. The loss of volume due to wetting of the skin was negligible, less than 1%. Both solutions were then titrated for chlorine with sodium thiosulfate, (the chloride reduction by the thiosulfate being quantitative in aqueous solution) after the additions of hydrochloric acid and potassium iodide. The solution in which the hand and forearm had been exposed lost approximately 20%, i.e. about 9 milligrams, of the chlorine, showing selective uptake and retention of chlorine by the skin.

Experiment II

Experiment I was repeated using solutions containing typical chlorine concentrations of swimming pool water, namely 3 ppm and 0.6 ppm chlorine (as NaOCl). Once again, about 20% of the chlorine was selectively removed in both cases from the solution and retained by the skin, that is about 1.8 mg $Cl_2$ and 0.36 mg $Cl_2$ respectively.

In general, chlorine saturated hairy skin, after swimming, holds about 0.3 to no more than about 2.0 mg chlorine per square foot of exposed skin area.

Experiment III

Experiment I was repeated, except that this time, the hand and the forearm, after the exposure to the hypochlorite solution, were contacted for 30 seconds with three liters of solution of sodium thiosulfate, containing 0.021 g/l of sodium thiosulfate, that is the stoichiometric amount of thiosulfate needed to reduce the retained chlorine on the skin (about 9 mg) to chloride. We found that only a negligible amount of the chlorine on the skin was reduced as nearly all of the thiosulfate in the solution remained unreacted after the immersion, as shown by titration with iodine. In contrast, the same amount of chlorine in aqueous solution is stoichiometrically reduced by thiosulfate (see Experiment I above).

Experiment IV

The hand and forearm, after the attempted reducing treatment of Experiment III were again contacted with a solution of sodium hypochlorite, exactly as described in Experiment I. This time, there was no further removal of chlorine from the hypochlorite solution, confirming (i) that the skin was still saturated with chlorine, despite the "stoichiometric" thiosulfate treatment; and (ii) that chlorine saturation of the skin is determined by the chlorine concentration of the water in the presence of a large excess of chlorinated water, as is the case in swimming pools.

The following Examples 1-3, taken in combination with Experiments I-IV, illustrate typical methods of practicing our invention, it being understood that many variations will occur to one skilled in the art without departing from the scope of the invention as defined in the appended claims.

Example 1

Experiment III was repeated, except this time, ten times the stoichiometric amount of our preferred reducing agent, sodium thiosulfate, was used. Under these conditions, rapid (10 to 30 seconds) total chlorine reduction to chloride was found. This was demonstrated by titrating the remaining thiosulfate with iodine, and also conformed by repeating experiment IV where, (instead of substantially no chlorine uptake) this time approximately 20% chlorine uptake by the skin occurred again in the second immersion.

This experiment was repeated with five times the stoichiometric amount of thiosulfate. Under this condition total chloride reduction took one minute.

EXAMPLE 2

Experiment I was repeated, and the amount of chlorine uptake by the skin was again measured by analysis of the residual chlorine in the hypochlorite solution. After the contact immersion, the skin was washed vigorously with soap and warm water. After this wash the affected skin area was analyzed for retained chlorine by removing the chlorine from the skin with a tenfold stoichiometric excess of sodium thiosulfate as in Example 1. Clearly, substantially all of the chlorine that had been retained by the skin had been unaffected by the soap wash.

Example 3

Example 1 was repeated with other typical reducing agents, namely sodium nitrite, sodium sulfite and ascorbic acid respectively. In each case, five to ten times the stoichiometric amount of each of the reducing agents was again required for effective and similarly rapid removal of chlorine retained by the skin. Free (i.e. uncombined) urea was also found to be effective, but, with immersion times of 30 seconds in a urea solution, here 50 times the stoichiometric amount of free urea was required. The need for this large excess was found to be due to a kinetic effect, in that a longer immersion (5 minutes) of skin in a urea solution resulted in a lower urea requirement for total chlorine reduction and removal from the skin, namely approximately 20 times the stoichiometric requirement. Urea compounds such as clathrates are too slow for practical purposes.

We have thus found that, surprisingly, we can remove rapidly the strongly held chlorine from human skin and hair, previously exposed to chlorinated water such as swimming pool water by contacting, as by immersion or washing, the skin and/or hair with water and with a suitable water-soluble reducing agent provided in amount several times, and preferably at least five times in excess of the stoichiometric requirement of the chlorine removal by such contacting requiring from about 10 seconds to no more than about 5 minutes.

An essential feature of the invention is thus the use, in the absence of soap or detergent, of at least a five-fold stoichiometric excess of a suitable reducing agent over the tightly held chlorine selectively removed from swimming pool water by human skin and/or hair. While the skin area and hairiness vary widely with age, height and weight and other characteristics of the swimmer, a range of not less than about 6 mg and no more than about 80 mg chlorine retained per swimmer (equivalent to about 20-40 sq. ft. of hairy skin per swimmer) is adequate and wide enough to encompass most swimmers. Thus, for any given reducing agent the requirement of an excess of at least five times stoichiometric is easily determined; for example, in the case of the preferred sodium thiosulfate, as $Na_2S_2O_3$, $(158/35.5 \times 5) \times 0.006 = 0.0133$ grams to $(158/35.5 \times 5) \times 0.05$ grams $= 1.78$ grams cover the above range. For practical purposes, 1 gram of sodium thiosulfate per swimmer is usually more than adequate.

We have further found, surprisingly, that the admixture of lesser than the above critical amounts, though still several times in excess of the stoichiometric amount, of such suitable reducing agents with solid or aqueous toilet soaps, and with aqueous detergent-containing liquids, herein referred to as shampoos, permits effective removal of chlorine from skin and hair when the skin and/or hair are "soaped" or "shampooed" for the same short time periods, provided that, the reducing agent is chemically unaltered in the admixture, that is, the reducing agent is not chemically reacted and thereby rendered ineffective either with the soap or with the detergent or with any other common additive such as free fatty acid, perfumes and the like. Specifically, we have found that a toilet soap or shampoo composition comprising as little as three-fold stoichiometric excess of a suitable reducing agent is sufficient to remove chlorine rapidly from skin and hair, and that such a composition is not toxic and does not irritate or harm the skin or hair nor adversely affect the soap's or the shampoo's normal cleansing and lathering action, and at the same time avoids the waste of soap or shampoo which results from repeated and excessive scrubbing in unsuccessful attempts to rid oneself of the chlorine in the absence of the appropriate reducing agent. While we do not wish to be held to any theory it is plausible to attribute the more effective reducing action to the enhanced wetting of skin and hair due to the surfactant action of the soap or detergent. As used herein, the terms toilet soap and detergent have their accepted meanings as defined, for example, in "The Chemical Process Industries", by R. Norris Shreve, McGraw-Hill Book Company, Inc. 2nd Edition (1956) page 628 and pages 629-635, respectively. A suitable definition for "soap" as used herein is, a cleaning and emulsifying agent made by the action of an alkali on fat or a fatty acid such as the sodium or potassium salt of a fatty acid. Typical examples of soaps useful in this invention include but are not limited to sodium oleate, sodium linoleate, sodium palmitate, sodium stearate, sodium linolenicate, sodium laurate, sodium capricate, sodium caproicate, sodium ricinoleate. Such soaps include common household hand and body soaps as customarily sold in supermarkets and the like.

A suitable definition for "detergent" as used herein is a synthetic water soluble cleansing preparation that emulsifies oils and holds dirt in suspension. Typical examples of detergents useful in this invention include but are not limited to pareth-15-9, lauramide DEA, cocamide DEA, polysorbate-80, sodium laureth sulfate, sodium lauryl sulfate, ammonium lauryl sulfate, amphoteric-1, TEA-lauryl sulfate, TEA-laureth sulfate.

A suitable reducing agent is a non-toxic and non-skin-irritating reducing agent that is compatible with toilet soap and/or detergent or the like, i.e. said agent is chemically non-reactive and non-interfering with the aforesaid soap's and/or detergent's cleansing and lathering characteristics, when said agent is used in the critical amounts required for the purpose of chlorine removal from skin and hair, either by itself or in admixture with soap and/or detergent. Preferably the reducing agent is highly soluble in water. Suitable inorganic reducing agents include alkali metal thiosulfates, alkali metal nitrites and alkali metal sulfites and the like with sodium thiosulfate being preferred because of its low cost and excellent shelf life. Useful reducing agents include but are not limited to the following: sodium thiosulfate, sodium sulfite, sodium hydrosulfite, urea, thiourea, sodium nitrite, ascorbic acid, hydrazine, hydroxylamine, pyrrole, sodium ferrocyanide, hydroquinone, formaldehyde, furfural, sodium hypophosphite.

Generally when we have compounded a suitable reducing agent with toilet soap by mixing and shaping into a solid such as a bar we have found that the amount, by weight, of reducing agent, expressed as percent by weight of the toilet soap, has to be at least 2% of sodium thiosulfate or its equivalent in reducing action to satisfy usually the requirement of providing at least a three-fold stoichiometric excess of reducing agent over the chlorine retained by a swimmer's skin and hair. This finding is more the result of practical experience with swimmers, then precise quantitative analytical data which can fluctuate widely with different individuals; but an "order-of-magnitude" indication of the relation between the toilet-soap composition and chlorine retained by a swimmer's skin and hair is as follows. Typically, a swimmer may soap himself with some 4 grams of solid soap when showering after a swim. With, for example, 4% of the preferred sodium thiosulfate as $Na_2S_2O_3$, he thus reduces the retained chlorine with 160 milligrams of the thiosulfate which is about a three-fold stoichiometric excess, when some 12 milligrams of chlorine were retained by his skin during the swim. Clearly, in the case of higher retained chlorine levels, more reducing agent is required, but in practice we have found an upper limit of 15%, by weight, of reducing agent, expressed as percent by weight of the toilet soap, to be generally effective as a rapid chlorine remover, and at the same time not affect the cleansing and lathering characteristics of the toilet soap nor significantly increase the amount of soap composition customarily used in showering after a swim.

The amounts of the reducing agent can vary greatly depending upon the particular reducing agent and the conditions under which it is used. For example, as the pH of the soap or detergent solution changes the amount of reducing agent necessary for use in particular composition will vary. At low pHs, ureas react more slowly, and therefore larger amounts of urea must be used when it is the reducing agent, as compared with sodium thiosulfate. Similarly with thiosulfates, there may be stability problems in specific pH ranges. Therefore thiosulfates are preferably used with soaps and detergents which have inherent pHs in the range of from about 5 to about 11. Thus there will be variations depending upon soap and detergent solutions as well as specific reducing agents.

It has been found that a mixture of reducing agents and particularly alkali metal thiosulfate and urea is preferred when used with soaps and shampoos in accordance with this invention. Sodium thiosulfate is found to react rapidly to reduce chlorine on the skin. Urea reacts less rapidly but has a greater action per unit weight than the sodium thiosulfate. By mixing the two in proportions of preferably 50 to 70% by weight of sodium thiosulfate to 50 to 30% by weight urea, one achieves rapid action to start the chlorine reduction followed by substantial reaction with urea to complete the chlorine reduction within a reasonable time period of wetting the skin.

In the following examples, we illustrate typical modes of preparing such toilet soap-reducing agent compositions, including experimental illustrations of the beneficial synergistic effect of the soap-reducing compositions vs. the use of a reducing agent in the absence of soap.

EXAMPLE 4

9.2 grams of granulated toilet soap (solids consisting of more than 99% of alkali salt of fatty acids, and about 8% by weight water) were mixed thoroughly at room temperature with 2 milliliters of sodium thiosulfate solution containing 0.8 grams of sodium thiosulfate until a uniform mixture was obtained. About 4 milliliters of distilled water was added turning the mixture into a stiff batter. The batter was shaped into a bar and allowed to dry at room temperature for one day before being used. The bar contained about 8% of thiosulfate.

Three swimmers, after exposure to relatively heavily chlorinated poolwater containing one ppm chlorine, removed the chlorine from their skin and hair (using the same bar by soaping themselves in succession for three minutes each) and then showering.

EXAMPLE 5

A soap bar was prepared as in Example 4, except that 0.6 grams of sodium thiosulfate was combined with 9.4 grams of granulated toilet soap. This bar, containing about 6% sodium thiosulfate was effective when used, as in Example 4, by three swimmers after exposure to chlorinated pool water containing one ppm chlorine.

EXAMPLE 6

0.4 milliliters of urea solution in water, containing 0.2 grams of dissolved urea were mixed with 9.8 grams of the granulated toilet soap of Example 4 and shaped into a bar, as in Example 4. The three swimmers exposed themselves to swimming pool water containing two ppm of chlorine. The urea-soap bar, containing 2% of urea removed chlorine from the three swimmers after each soaped himself for three minutes and then showered. About 70 milligrams of urea reduced on the order of 12–15 milligrams of retained chlorine from each swimmer in three minutes, (as determined by the absence of chlorine odor) thus demonstrating that a stoichiometric excess of about twenty time was effective in the presence of the toilet soap, whereas the much larger excess shown in Example 3 (50 times) was required in the absence of soap to effect rapid chlorine removal. To further demonstrate the effectiveness of the soap-reducing agent combination, the experiments of Example 3 were repeated, except that the hairy forearm and hand were soaped with 0.75 grams of the urea-soap of this Example, providing an excess of urea of about twenty times. The chlorine retained by the forearm and hand was reduced substantially completely in thirty seconds.

Similar results as in Examples 4 and 6 were obtained with soaps compounded with other suitable reducing agents, including alkali nitrites, sulfites and ascorbic acid, used in amount between 2% and 15% by weight, as above.

The addition of a suitable water-soluble reducing agent to detergent-containing liquid aqueous shampoos, such as common hair or baby shampoos, results in the same rapid and enhanced chlorine reduction as the admixture of the reducing agent with solid toilet soap or aqueous solutions thereof, as illustrated by the following examples.

EXAMPLE 7

Eight milliliters of sodium thiosulfate solution containing 0.4 grams $Na_2S_2O_3.5H_2O$/milliliter were mixed with 50 milliliters of a typical commercial aqueous shampoo comprising a mixture of detergents, about 21% by weight, including sodium laureth sulfate and lauramide DEA, in addition to sodium chloride, formalin, and fragrance and coloring. The term "laureth" is an FDA approved name for a commercially available mixture of polyoxyethylene lauryl ethers. "Lauramide" is an amide of dodecanoic acid. This liquid composition thus contained 15% sodium thiosulfate, pentahydrate expressed as percent of detergent all by weight. 15 milliliters of the above composition reduced (no chlorine odor), in one minute, the four milligrams of chlorine retained by a swimmer's hair after the hair was exposed to water containing five ppm chlorine.

EXAMPLE 8

The baby shampoo of Example 7 was mixed with only 6 milliliters of the sodium thiosulfate solution of Example 7 (12 weight % based on detergent content) and again successfully tested as in Example 7 resulting in chlorine-free, odorless hair in one minute, the hair having been exposed to pool water containing one ppm chlorine.

Three milliliters of this Example's shampoo solution were used also on the forearm and hand previously contacted with the hypochlorite solutions of Experiment 2, as in Example 2. A stoichiometric excess of thiosulfate of only 300% in the presence of the shampoo's detergent, was ample to remove the chlorine from the forearm and hand in twenty seconds, illustrating the benefit of the presence of the detergent.

EXAMPLE 9

The baby shampoo of Example 7 was mixed with only 1 milliliter of sodium thiosulfate pentahydrate to yield a product containing 2% by weight, relative to the detergent content. This product was successfully tested resulting in chlorine-free odorless hair in one minute, the hair having been exposed to pool water containing 1 ppm chloride.

In general, in the case of liquid aqueous shampoos, the synergistic effect has been found to be the same as with toilet soap, that is the critical amounts of reducing agent again is provided in amount between 2% and 15% of the contained detergent, all by weight, as above.

EXAMPLE 10

A 3 liter solution of water containing 15 ppm of chlorine was prepared as in Experiment 1. In this solution a hand and hairy forearm were immersed at room temperature for 30 seconds, then removed from the solution. The solution was then titrated for chlorine, and as in previous examples, approximately 20% of the chlorine was found to have been removed from the solution.

Next, the rinsed hand and forearm were immersed for 30 seconds in 3 liters of a solution of water containing the stoichiometric amount of thiosulfate needed to reduce the retained chlorine on the skin to chloride. We found that less than 14% of the chlorine was reduced.

The same sequence of tests was repeated, this time using a stoichiometric amount of urea in solution to attempt to reduce the skin-retained chlorine to chloride. After 30 seconds, titration showed virtually no chlorine reduction had occurred.

The sequence was repeated a third time, but in this instance, stoichiometric quantities of both thiosulfate and urea were added to the 3 liter solution. Instead of getting only about a 14% chlorine reduction, which would have been predicted from the previous tests, approximately 42% of the retained chlorine was reduced. Surprisingly, there is an enhanced effect due to the combination of these reducing agents.

EXAMPLE 11

Example 10 was repeated with this difference: the chlorine-saturated hand and forearm were immersed in solutions of reducing agents to which approximately 20 g. of granulated soap had been added, "Ivory" soap powder a trademarked product of Proctor and Gamble Company of Cincinnati, Ohio, containing sodium cocoate and sodium tollowate.

A stoichiometric solution of sodium thiosulfate with soap reduced approximately 15% of the skin-retained chlorine. A stoichiometric solution of urea with soap added reduced approximately 15% of the skin-retained chlorine (showing an enhanced reducing effect due to the soap). But a solution of stoichiometric quantities of both sodium thiosulfate and urea with soap added reduced approximately 50% of the skin-retained chlorine. As in the previous example, there is an unexpectedly enhanced effect due to the combination of these reducing agents. When a synthetic detergent is used in place of soap, advantageous results are also obtained. This example of a soap or synthetic detergent with a mixture of urea and alkali metal thiosulfate in varying proportions is found to best achieve the objects of this invention in permitting removal of chlorine from the skin and hair. The smallest amount of reducing agent and most rapid times of cleaning are achieved with these mixtures.

EXAMPLE 12

The following ingredients were mixed in the amounts by weight noted below:
water: 76.15
sodium laureth sulfate: 12%
lauramide DEA: 4%
S.D. alcohol 3A: 2.6%
urea: 2.5%
sodium thiosulfate: 1%
glycol stearate: 1.5%
fragance (PFW #800471): 0.25%.

An effective shampoo in accordance with this invention is thus formed.

EXAMPLE 13

The following ingredients were mixed in the amounts by weight noted below:

Water: 9%
sodium tallowate/cocoate: 85%
urea: 3%
sodium thiosulfate: 1%
lanolin: 0.5%
titanium dioxide: 1%
fragrance (PFW #800471): 0.5%.

An effective soap in accordance with this invention is thus formed.

The other above-described reducing agents are equally suitable for addition to shampoos containing soap or detergent, with similar beneficial results. Mixtures of more than one soap, more than one reducing agent and/or more than one detergent can be used as at least the equivalent of a single soap or the like in particular formulations to give at least equivalent actions.

The soaps, detergents and shampoos of the present invention can be in liquid or solid form as known in the art. Shampoos are normally in liquid form and contain known detergents. The soaps are often used in solid bar or powder form as known in the art. Typical additives to soap include fragrances such as PFW #800471 from Pollak's Fruital Works, Inc. of Middletown, New York, and Fragrance #32-329 from Alpine Aromatics International, Inc. of Metuchen, New Jersey.

Other additives include whitening or coloring agents such as titanium dioxide; emollients such as lanolin or octyl hydroxystearate; and preservatives such as Trisodium HEDTA and BHT.

Typical additives to shampoos include fragrances such as the ones noted above; solubilizers such as SD alcohol 3A; conditioners such as glycol stearate and hydrolyzed animal protein; and preservatives such as formaldehyde, methylparaben, and propylparaben.

The fragrances are normally used in amounts of from 0.1% to 5% by weight, coloring agent 0.4 to 8% by weight, emollients 0.4% to 15% by weight and preservatives 0.4 to 3% by weight of the total composition. The specific percentages can vary greatly and in many cases one or more of the above additives can be and often are omitted.

The art-recognized terms such as SD alcohol 3A and the like are well-known and found in The Cosmetics, Toiletries and Fragrance Association Dictionary 2nd Edition.

Many variations, especially with respect to the selection of suitable reducing agents other than those specifically named herein are considered within the scope of the invention.

What is claimed is:

1. A toilet soap composition for cleansing and removing retained chlorine from human skin and hair after immersion in chlorine containing waters, said composition consisting essentially of a chemically stable, uniform mixture of a toilet soap and a water soluble, non-toxic and harmless-to-the skin chlorine-reducing agent which is a mixture of from about 50 to about 30% by weight urea and from about 50 to about 70% by weight of an alkali metal thiosulfate, said agent being present in said mixture in amount between at least about 2% and less than about 15% by weight of said soap in said mixture and being compatible with said soap.

2. A liquid aqueous shampoo composition for cleansing and removing retained chlorine from human skin and hair after immersion in chlorine containing waters, said composition consisting essentially of a chemically stable, uniform mixture of a detergent and a water soluble, non-toxic and harmless-to-skin chlorine-reducing agent which is selected from the group consisting of urea and mixtures of urea and an alkali metal thiosulfate, said agent being present in amount between 0.4% and 6% of said liquid composition and about 2% to 15% of said contained detergent and being compatible with said shampoo compositions.

3. A method of rapidly removing chlorine from human skin and hair after immersion in chlorine containing waters, said method comprising contacting said skin and hair with a toilet soap or detergent composition and water, said composition comprising a chemically stable uniform mixture of toilet soap or detergent and a water-soluble, non-toxic and harmless-to-the skin chlorine-reducing agent, said agent being provided in amount at least three times the stoichiometric amount required to reduce said chlorine to chloride and being compatible with said soap or detergent.

4. The method of claim 3 wherein said mixture is provided as an aqueous solution.

5. A method in accordance with the method of claim 3 wherein
said chlorine reducing agent is sodium thiosulfate.

6. A method in accordance with the method of claim 3 wherein
said detergent composition or soap is in the form of a shampoo composition and said chlorine reducing agent is sodium thiosulfate.

7. A method in accordance with the method of claim 3 wherein said chlorine-reducing agent is a mixture of an alkali metal thiosulfate and urea.

8. A method in accordance with the method of claim 3 wherein said chlorine-reducing agent is urea.

9. A method in accordance with the method of claim 3 wherein said skin and hair is contacted with a toilet soap with said chlorine reducing agent being present in an amount of between about 2 and less than 15% by weight of said soap.

10. A method in accordance with the method of claim 9 wherein said chlorine reducing agent is selected from the group consisting of alkali metal thiosulfates, alkali metal nitrites, alkali metal sulfites, ascorbic acid and urea.

* * * * *

UNITED STATES PATENT AND TRADEMARK OFFICE
CERTIFICATE OF CORRECTION

PATENT NO. : 4,295,985
DATED : October 20, 1981
INVENTOR(S) : Henry G. Petrow and Mark L. Weissman It is certified that error appears in the above—identified patent and that said Letters Patent is hereby corrected as shown below:

Column 7, line 58, cancel "chloride" and substitute --chlorine--.

Signed and Sealed this

Ninth Day of February 1982

[SEAL]

Attest:

GERALD J. MOSSINGHOFF

Attesting Officer — Commissioner of Patents and Trademarks